United States Patent [19]

Messina et al.

[11] Patent Number: 4,981,963
[45] Date of Patent: Jan. 1, 1991

[54] METHOD OF PREPARATION OF OXALIC ACID ESTERS AND AMIDES

[75] Inventors: Giuseppe Messina, Alghero; Giovanni M. Sechi, Ozieri; Loreno Lorenzoni, Porto Torres; Giovanni Chessa, Sassari, all of Italy

[73] Assignee: Enichem Anic S.p.A., Palermo, Italy

[21] Appl. No.: 341,750

[22] Filed: Apr. 21, 1989

[30] Foreign Application Priority Data

Apr. 21, 1988 [IT] Italy .................................. 20274 A/88

[51] Int. Cl.$^5$ .................. C07D 279/12; C07D 265/30; C07C 67/20; C07C 231/08
[52] U.S. Cl. .......................................... 544/59; 544/63; 544/106; 544/382; 546/247; 548/245; 558/418; 560/190; 560/193; 560/196; 564/160
[58] Field of Search ........................ 560/190, 196, 193; 564/159, 160; 544/59, 63, 106, 382; 558/418; 546/247; 548/245

[56] References Cited

U.S. PATENT DOCUMENTS 4,447,639 5/1984 Sofranko et al. .................... 560/204

FOREIGN PATENT DOCUMENTS 0245631 11/1987 European Pat. Off. .
1668639 7/1971 Fed. Rep. of Germany .

OTHER PUBLICATIONS

Sorokina et al., Chemical Abstracts, vol. 77, No. 1, Jul. 1972, 5823v.

Primary Examiner—Werren B. Lone
Assistant Examiner—Vera C. Clarke
Attorney, Agent, or Firm—Oblon, Spivak, McClelland, Maier & Neustadt

[57] ABSTRACT

A new process is described for the preparation of oxalic acid esters and amides of general formula (I)

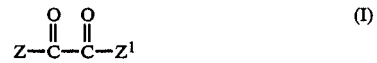

wherein
Z designates an —OR or —NR$^1$R$^2$ group, wherein R represents substituted or unsubstituted alkyl, alkenyl, cycloalkyl, aryl, or aryl-alkyl, R$^1$ is hydrogen or substituted or unsubstituted alkyl, alkenyl, cycloalkyl, aryl, or aryl-alkyl, R$^2$ represents substituted or unsubstituted alkyl, alkenyl, cycloalkyl, aryl, or aryl-alkyl, or R$^1$ and R$^2$ taken together with the adjacent nitrogen atom represent a saturated 5-, 6-, 7-, or 8-membered heterocyclic ring, which may contain an additional heteroatom selected from —O—, —S—, and —N(H, Alkyl)—, and optionally bear one or more alkyl or alkenyl substituents, and
Z$^1$ designates an —OR or —NR$^1$R$^2$ group, wherein R, R$^1$, and R$^2$ are as defined before, or a group —NHCOCH$_3$, which comprises the base-catalysed reaction of diacetyloxamide with an alcohol ROH or/and an amine HNR$^1$R$^2$. The compounds of formula (I) have many industrial utilities, mainly as intermediates and stabilizers in the polymer field.

16 Claims, No Drawings

METHOD OF PREPARATION OF OXALIC ACID ESTERS AND AMIDES

The present invention refers to a new process for the preparation of oxalic acid derivatives of general formula (I)

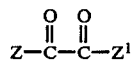 (I)

$$Z-\overset{O}{\underset{\|}{C}}-\overset{O}{\underset{\|}{C}}-Z^1$$

wherein

Z designates an —OR or —NR$^1$R$^2$ group, wherein R represents substituted or unsubstituted alkyl, alkenyl, cycloalkyl, aryl, or aryl-alkyl, R$^1$ is hydrogen or substituted or unsubstituted alkyl, alkenyl, cycloalkyl, aryl, or aryl-alkyl, R$^2$ represents substituted or unsubstituted alkyl, alkenyl, cycloalkyl, aryl, or aryl-alkyl, or R$^1$ and R$^2$ taken together with the adjacent nitrogen atom represent a saturated 5-, 6-, 7-, or 8-membered heterocyclic ring, which may contain an additional heteroatom selected from —O—, —S—, —N(H,alkyl)—, and optionally bear one or more alkyl or alkenyl substituents, and Z$^1$ designates an —OR or —NR$^1$R$^2$ group, wherein R, R$^1$, and R$^2$ are as defined before, or a group —NHCOCH$_3$. For the purposes of the present application, the term "alkyl" both when it is used to identify a radical per se or the alkyl moiety in the "aryl-alkyl" radicals, designates a straight or branched alkyl radical, typically containing from 1 to 12 carbon atoms, which may be unsubstituted or bear one or more substituents. Substituents which do not negatively interfere with the reaction course and can therefore be present are for instance amino, mono-alkylamino, dialkylamino, hydroxy, alkoxy, carboxy, carbalkoxy, formyl, mercapto, alkylthio, cyano, nitro, halogen, etc..

Analogously, the term "alkenyl" represents a straight or branched alkenyl radical, containing from 3 to 12 carbon atoms, which may be unsubstituted or bear one or more substituents such as those listed above, and may contain more than one double bond.

The term "cycloalkyl" designates a saturated 5- to 12-membered cycloaliphatic ring.

Finally, the term "aryl" as well as the aryl portion in the "aryl-alkyl" groups, represents an optionally substituted mono-, bi-, or tri-cyclic aromatic radical containing from 6 to 14 carbon atoms. As an example, substituents which may be present on the ring are those listed before, as well as alkyl, halo-alkyl, hydroxy-alkyl, etc..

The oxalic acid derivatives of formula (I), are known compounds, widely described in literature, which have many industrial uses.

In particular, as an example, those compounds of formula (I) wherein Z and Z$^1$ are —NR$^1$R$^2$ groups, wherein at least one of R$^1$ and R$^2$ represents an amino- or hydroxy-substituted alkyl group, are useful as intermediates in the preparation of polyamides or as additives or co-polymer in the preparation of special polymers (C.A. 96 : 20535p; C.A. 78 : 99149a; C.A. 83 : 148028z; C.A. 77 : 5823v; C.A. 103 : 38155n); those compounds of formula (I) wherein Z is —OR wherein R is alkyl and Z$^1$ is —NR$^1$R$^2$ wherein R$^1$ is hydrogen and R$^2$ is a substituted phenyl group, showed to be useful as antiallergics and immunomodulators (C.A. 106 : 138091u); oxalylanilides of formula (I) wherein Z and Z$^1$ represent —NR$^1$R$^2$ groups wherein R$^1$ is hydrogen or methyl and R$^2$ is an optionally substituted phenyl group, showed to be useful as pesticides (C.A. 103: 141636u); etc..

The methods most widely known in literature for the preparation of the oxalic acid derivatives of formula (I), involve the use of highly toxic reactants, such as oxalic acid or oxalyl chloride, or, in the preparation of oxamide derivatives, of oxalic acid esters, typically diethyl oxalate, an expensive reactant, which in its turn is prepared from oxalic acid or oxalyl chloride.

An alternative method for the preparation of some oxamide derivatives is described in European patent publication no.245631, and involves the reaction of oxamide with some particular diamino or hydroxyamino derivatives, under fairly drastic reaction conditions. It has now been found, and represents the object of the present invention, that it is possible to prepare a wide class of oxalic acid derivatives, including both esters and amides, as well as mixed ester/amides, under substantially mild reaction conditions, through base-catalysed reaction of diacetyloxamide (II)

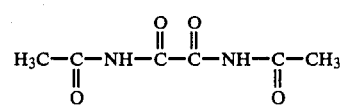 (II)

$$H_3C-\overset{O}{\underset{\|}{C}}-NH-\overset{O}{\underset{\|}{C}}-\overset{O}{\underset{\|}{C}}-NH-\overset{O}{\underset{\|}{C}}-CH_3$$

with the corresponding alcohol ROH or/and the corresponding amine HNR$^1$R$^2$.

In particular, the process of the present invention may be employed for preparing those compounds of formula (I) wherein Z is as defined above and Z$^1$ represents an —NHCOCH$_3$ group, by reacting diacetyloxamide with an equimolar amount or a slight excess of the corresponding alcohol ROH or amine HNR$^1$R$^2$. In the actual practice, in this case, the reaction is carried out by contacting diacetyloxamide with the suitably selected reaction partner, in the presence of an organic solvent which is capable of dissolving the starting diacetyloxamide, such as dimethylacetamide or dimethylformamide, or in the presence of an organic solvent which is capable of dissolving the diacetyloxamide reaction partner and the reaction product. Solvents suitable for this last purpose are for instance polar, protic or aprotic, solvents such as cyclic ethers (e.g. tetrahydrofuran, dioxane), aliphatic ethers (e.g. diethylether, diisopropylether), dietherated glycols (e.g. ethylene glycol dimethyl ether), halogenated aliphatic hydrocarbons (e.g. chloroform, dichloroethane, methylene chloride), organic acid esters (e.g. ethyl acetate, ethyl propionate), and lower alkanols (e.g. methanol, ethanol, isopropanol).

The reaction may be carried out at a temperature of from 0° and 230° C., but preferably of from 10° to 100° C., and even more preferably of from 10° to 80° C. Surprisingly, in fact, the reaction of diacetyloxamide with alcohols and amines may be directed selectively toward the oxalyl radical.

The reactivity of the diacetyloxamide oxalamide bond is in fact quite different from the reactivity of the acetamido bond, so that working under mild conditions, at room temperature or at a slightly higher temperature, the desired products can be obtained as pure products and in very high yields.

The reaction pressure is generally the atmospheric pressure, even if sometimes higher pressures can be employed advantageously, particularly when the diacetyloxamide reaction partners have low boiling points.

The reaction must be carried out in the presence of a basic catalyst. When the reaction partner of diacetyloxamide is an amine $HNR^1R^2$, it is this last compound which autocatalyses the reaction, while when the reaction partner of diacetyloxamide is an alcohol ROH, a basic catalyst must necessarily be added to the reaction mixture. Said basic catalyst can be suitably selected from alkaline alkoxides, e.g. sodium methoxide and ethoxide, and the N-containing organic bases, preferably tertiary N-containing organic bases, e.g. triethyl- or trimethyl-amine, pyridine or picoline. The basic catalyst may suitably be employed in a molar amount, per mole of starting diacetyloxamide, of from 0.0001 to 0.5, and preferably from 0.001 and 0.1.

Once the desired compound of formula (I) is obtained wherein Z is as defined above and $Z^1$ is a group $-NH-COCH_3$, it is possible to replace the acetamido group with an $-OR$ or $-NR^1R^2$ group, through base-catalysed reaction of the obtained compound with the suitably selected alcohol or amine, thus allowing preparation of compounds of formula (I) wherein Z and $Z^1$ are different and $Z^1$ is different from $-NHCOCH_3$.

Again, by the same reaction, but starting from diacetyloxamide and an at least double molar amount of alcohol or amine, under the same reaction conditions described above, the symmetrical compounds of formula (I) wherein Z and $Z^1$ are the same, are obtained. Generally, in this last case, excess alcohol or amine is preferably employed, and even more preferably, a strong excess. In some cases the excess of starting alcohol or amine may also act as the reaction medium, and in this case the use of an additional organic solvent may be avoided.

Finally those compounds of formula (I) wherein one of Z and $Z^1$ is an $-OR$ group and the other is an $-NR^1R^2$ group, may simply be prepared by reacting diacetyloxamide with equimolar amounts, or a slight excess, of both the amine $HNR^1R^2$ and the alcohol ROH. In this case, the amine also acts as the basic catalyst and no additional base is required.

When the compound of formula (I) which forms in the reaction contains a group $-OR$ or $-NR^1R^2$, wherein at least one of R, $R^1$ and $R^2$ bears an hydroxy, amino, or alkylamino substituent, this compound may react, in suitable conditions, with another molecule of diacetyloxamide and the thus obtained condensation product may in its turn react with another molecule of the first compound, thus affording oligomerization and/or polymerization products.

The process leading to the formation of said oligomers or polymers obviously falls within the scope of the present invention.

Diacetyloxamide reaction partners of particular interest for the application of the present invention are:
(a) alcohols of formula ROH wherein R represents
  a straight or branched, unsubstituted, alkyl or alkenyl radical,
  a straight or branched alkyl or alkenyl radical bearing one or more groups independently selected from alkoxy, alkylthio, mercapto, halogen, nitro, hydroxy, di-alkylamino, carboxy and oxo,
  a phenyl radical optionally substituted with one to three groups independently selected from alkyl, alkoxy, halogen, hydroxy, mercapto, alkyl-thio, hydroxy-alkyl, halo-alkyl, di-alkyl-amino, and nitro,
  a phenyl-$(C_1-C_4)$alkyl radical wherein both the alkyl and phenyl groups may be substituted as above;
(b) primary or secondary amines of formula $H_2NR^2$ or $HNR^1R^2$, wherein $R^1$ and $R^2$, each independently, represent
  an unsubstituted, straight or branched, alkyl or cycloalkyl radical,
  a straight or branched alkyl or a cycloalkyl radical substituted with one or more groups independently selected from hydroxy, alkoxy, amino, mono-alkylamino, di-alkylamino, halogen, nitro, mercapto, alkyl-thio, carboxy, and oxo,
  a phenyl radical optionally substituted with 1 to 3 groups independently selected from alkyl, alkoxy, halogen, hydroxy, amino, mercapto, alkyl-thio, mono-alkyl-amino, di-alkyl-amino, hydroxy-alkyl, halo-alkyl, and nitro,
  a phenyl-$(C_1-C_4)$alkyl radical wherein both the alkyl and phenyl radical may be substituted as above,
  or $R^1$ and $R^2$ taken together with the adjacent nitrogen atom represent a saturated 5-, 6-, 7-, or 8-membered heterocyclic ring which may be alkyl- or alkenyl-substituted, and may contain an additional heteroatom selected from $-O-$, $-S-$, and $-N(H \text{ or Alkyl})-$. In more detail, alcohols of particular interest as diacetyloxamide reaction partners are, for instance, methyl alcohol, ethyl alcohol, isopropyl alcohol, cyclohexyl alcohol, ethylen-glycol, 2-methoxy-ethanol, phenol, benzyl alcohol, and the like alcohols.

Amines which can suitably be employed are, for instance, methylamine, ethylamine, n-propylamine, sec-butylamine, tert-butylamine, cyclohexylamine, ethanolamine, propanolamine, thioethanolamine, 2-methyl-thio-ethylamine, ethylendiamine, hexamethylendiamine, 2,3-dimethyl-1,4-butylendiamine, 2,3-dicyclohexyl-1,4-butylendiamine, tetramethylendiamine, 1,4-cyclohexyl-diamine, trimethylendiamine, 1,2-cyclohexyl-diamine, aniline, 4-chloro-aniline, 2-nitro-aniline, 2-hydroxy-benzylamine, benzylamine, phenethylamine, N-phenyl-ethanolamine, piperidine, morpholine, thiomorpholine, piperazine, N-methyl-piperazine, 1,2-isooxazolidine, 1,2-oxazine, etc.

The following examples which are only aimed at illustrating the process of the invention in more detail, must not be interpreted as a limitation to the scopes of the invention itself.

EXAMPLE 1

Preparation of oxalic acid diethyl ester

Absolute ethyl alcohol (320 ml) and N,N'-diacetyloxamide (50 g, 0.29 mol) are charged into a 500 ml-flask equipped with a condenser, a magnetic stirrer, a thermometer and an inlet tube for nitrogen. The reaction mixture is heated to the reflux temperature and sodium methoxide (0.0185 mol) is added thereto. About 30 minutes later the reaction mixture clears up. After additional 4 hours ethyl alcohol is distilled off. The residue is extracted with ethyl ether and the ether phase is washed with a small amount of water to remove any acetamide. The organic phase is dried over $Na_2SO_4$ and the solvent is removed by distillation affording a residue (40.3 g, 0.28 mol, 95% yield) of ethyl oxalate.

EXAMPLE 2

Preparation of oxalic acid diallyl ester

Allyl alcohol (42.5 g, 0.73 mol), N,N'-diacetyloxamide (10 g, 0.058 mol), and sodium methoxide (0.2 g, 3.7 mmol) are charged into a three-necked flask equipped with a reflux condenser, a magnetic stirrer, an inlet tube for nitrogen, and a thermometer. The temperature is brought to 75° C. and, after about 1 hour, clarification of the reaction mixture is noticed. The reaction is continued for additional 4 hours and allyl alcohol is then distilled off. The acetamide which precipitates is removed by filtration and the filtrate is then extracted with ethyl ether. The ether phase is washed with a very small amount of water to remove any acetamide, dried over $Na_2SO_4$ and evaporated off yielding the compound of the title (8.9 g, 0.052 mol, 90% yield). The product has been identified by comparing its I.R. spectrum with that reported in literature.

EXAMPLE 3

Preparation of N,N'-diphenyloxamide

Aniline (50 ml, 0.549 mol) and N,N'-diacetyloxamide (5 g, 0.029 mol) are charged into a three-necked flask equipped with a condenser, a magnetic stirrer, an inlet tube for nitrogen and a thermometer. The temperature is brought to 50° C. while vigorously stirring and after 2 hours the reaction is stopped by removing the heating bath.

The precipitate which forms is recovered by under vacuum filtration, washed with methanol and dried in the oven at 70° C., yielding the compound of the title (6.2 g, 0.026 mol, yield 89%) with m.p. 251°–4° C. (lit. 252°–4° C.). The structure of the product has been confirmed by comparing its I.R. spectrum, and in particular the characteristic bands at 3300 cm$^{-1}$ ($\gamma_{NHCO}$ stretching) and 1670 cm$^{-1}$ ($\gamma_{CO}$ stretching), with those reported in literature (Sadtler catalogue).

Elemental analysis: Calculated for $C_{14}H_{12}N_2O_2$; C 70.0%; H 5.0%; N 11.67%; Found: C 70.1%; H 4.9%; N 11.80%.

EXAMPLE 4

Preparation of N,N'-bis(n-butyl)oxamide

N,N'-diacetyloxamide (20 g, 0.116 mol) and anhydrous methyl alcohol (100 ml) are charged into a flask equipped with a reflux condenser, a dropping funnel, a thermometer, an inlet tube for nitrogen and a magnetic stirrer.

The temperature is brought to 5° C. with an ice-bath and a solution of n-butyl-amine (25 ml, 0.253 mol) in anhydrous methyl alcohol (25 ml) is dripped in. The reaction is exothermic and dripping is adjusted to keep the temperature below 10°–12° C. When all the methyl alcohol solution of the amine has been added, the reaction mixture has a jelly appearance.

The reaction mixture is then heated for ½ hour to 70° C., while the solution clears up, then it is poured over ice/water (150 ml) and the precipitate is recovered by filtration. The compound of the title is thus obtained (21.4 g, 0.107 mol, yield 92%) with m.p. 151°–2° C. (Lit. 150°–2° C.).

The I.R. spectrum of the compound shows the following characteristic absorption bands: 3299 cm$^{-1}$ ($\gamma_{NHCO\ stretching}$), 2956–2873 cm$^{-1}$ ($\gamma_{CH_3\ and_2\ CH}$ stretching), 1651 cm$^{-1}$ ($\gamma_{CO}$ stretching).

Elemental analysis: Calculated for $C_{10}H_{20}N_2O_2$; C 60.0%; H 10.0%; N 14.0%;

Calculated for C H 10.0%; N 14.0%; Found: C 59.9%; H 10.0%; N 13.97%.

EXAMPLE 5

Preparation of N,N'-bis(isopropyl)oxamide

The compound of the title (18 g, 0.105 mol, yield 90%) is obtained by following the procedure of the foregoing example but using isopropylamine (25 ml, 0.29 mol) instead of n-butylamine.

M.p. 213°–6° C. (from acetone)(Lit. 212°–5° C.).

Elemental analysis: Calculated for $C_8H_{16}N_2O_2$; C 55.81%; H 9.30%; N 16.27%; Found: C 55.60%; H 9.27%; N 16.30%.

EXAMPLE 6

Preparation of N,N'-bis-(2-hydroxyethyl)oxamide

A suspension of N,N'-diacetyloxamide (10 g, 0.058 mol) in anhydrous methyl alcohol (50 ml) is charged into a four-necked flask equipped with a reflux condenser, an inlet tube for nitrogen, a dropping funnel, a thermometer, and a magnetic stirrer. A solution of monoethanolamine (8.2 g, 0.134 mol) in anhydrous methyl alcohol (20 ml) is gradually dripped in at 25° C. The reaction is exothermic and the temperature rises up to 60° C. The reaction is allowed to proceed at this temperature for 2 hours, then the reaction mixture is cooled and the precipitate is recovered by filtration. The compound of the title is thus obtained (9.5 g, 0.054 mol, 93% yield) with m.p. 166°–69° C.

Elemental analysis: Calculated for $C_6H_{12}N_2O_4$; C 40.91%; H 6.82%; N 15.90%;

Calculated for C C 40.91%; H 6.82%; N 15.90%. Found: C 41.0%; H 6.9%; N 15.9%.

EXAMPLE 7

Preparation of oxalyl-bis-piperidine

A suspension of N,N'-diacetyloxamide (10 g, 0.058 mol) in ethyl alcohol (20 ml) is charged into a three-necked flask equipped with a reflux condenser, an inlet tube for nitrogen, a dropping funnel, and a magnetic stirrer. 98 % Pyridine (40 ml, 0.40 mol) is then dripped therein at 70° C., and after 40 minutes the complete solving of N,N'-diacetyloxamide in the reaction mixture is observed. The temperature is brought to 95° C. and kept at this value for 6.5 hours. Then water (60 ml) and chloroform (60 ml) are added to the reaction mixture and the organic phase is separated. Chloroform is distilled off and ethyl ether (30 ml) is added to precipitate the compound of the title. The precipitate is recovered by filtration and dried, thus affording the compound of the title (5.1 g, 0.023 mol, yield 39.2%) with m.p. 88°–90° C.

Elemental analysis: Calculated for $C_{12}H_{20}N_2O_2$; C 64.29%; H 8.9%; N 12.50%; Found: C 64.0%; H 8.80%; N 12.40%.

I.R. spectrum of the compound shows the following characteristic absorption bands: 2991 cm$^{-1}$, 2932 cm$^{-1}$, 2856 cm$^{-1}$ ($\gamma_{CH_2}$ stretching), 1651 cm$^{-1}$ ($\gamma_{NCO}$ stretching).

EXAMPLE 8

Preparation of oxalic acid di-isopropyl ester

N,N'-diacetyloxamide (5 g, 0.029 mol), isopropyl alcohol (16 g, 0.266 mol) and sodium methoxide (0.1 g, 1.9 mmol) are charged into a 100-ml, three-necked, flask equipped with a reflux condenser, a thermometer, and an inlet tube for nitrogen.

The reaction mixture is heated to the reflux temperature and after 3 hours the mixture clears up. Excess isopropyl alcohol is removed by distillation under atmospheric pressure and the compound of the title is purified by under vacuum distillation (3 mmHg), obtaining 4.8 g (27.6 mol) of oxalic acid diisopropyl ester with b.p./$_{3\ mmHg}$ 41°–2° C., and a 95% yield based on the distilled product.

The product has been characterized by $^1$H-NMR and elemental analysis: Calculated for $C_8H_{14}O_4$; C 55.17%; H 8.0%; O 36.78%; Found: C 54.77%; H 8.24%; O 36.98%.

EXAMPLE 9

Preparation of oxalic acid diphenyl ester

N,N'-diacetyloxamide (10 g, 0.058 mol), phenol (27.91 g, 0.297 mol) and sodium methoxide (0.2 g, 3.7 mmol) are charged into a three-necked flask equipped with a reflux condenser, a thermometer, an inlet tube for nitrogen, and a magnetic stirrer. The temperature is brought to 130° C., and after two hours the complete disappearance of the N,N'-diacetyloxamide is observed. The reaction mixture is then cooled and ethyl ether (30 ml) is added thereto. The compound of the title is separated from the reaction mixture by crystallization, recovered by filtration and recrystallized from absolute ethyl alcohol, yielding 4.5 g (18.6 mmol) of oxalic acid diphenyl ester with m.p. 132°–5° C.

Elemental analysis: $C_{14}H_{10}O_4$; C 69.4%; H 4.1%; O 26.4%; Found: C 69.7%; H 4.1%; 0 26.1%.

The obtained compound has been characterized by comparing its I.R. spectrum with that of an authentic sample.

EXAMPLE 10

Preparation of ethyl 1-piperidin-glyoxylate

A suspension of N,N'-diacetyloxamide (10 g, 0.058 mol) in absolute ethyl alcohol (40 ml) is charged into a three-necked, 100-ml, flask equipped with a reflux condenser, an inlet tube for nitrogen, a dropping funnel, and a magnetic stirrer. 98% Piperidine (8.8 ml, 0.089 mol) is dripped in at 25° C., the temperature rises to 35° C. and N,N'-diacetyloxamide completely dissolves. The reaction mixture is then heated to 70° C. and after about 90 minutes it is allowed to cool down to room temperature. The compound of the title is then extracted therefrom by the addition of a water/chloroform mixture and recovery of the organic phase. The extraction is repeated twice and the two organic extracts combined are concentrated by distilling off chlorofom and water. The compound of the title (7.7 g, 0.042 mol, 71.5% yield) is then recovered therefrom still by distillation, at 170° C. and 15 mmHg. The product has been identified by comparing its I.R. spectrum, the most characteristic bands being at 2940 cm$^{-1}$, 2860 cm$^{-1}$ ($\gamma_{CH_3}$, $_{CH_2}$ stretching), 1730 cm$^{-1}$ ($\gamma_{COO}$ stretching) and 1645 cm$^{-1}$ ($\gamma_{CON}$ stretching), with that reported in literature.

EXAMPLE 11

Preparation of poly-butyl-oxalate

N,N'-diacetyloxamide (15.005 g, 0.0872 mol), 1,4-butanediol (23.694 g, 0.2638 mol), sodium methoxide (0.1 g, 1.9 mmol), and ethyl acetate (65 ml) are charged into a three-necked flask equipped with a reflux condenser, a thermometer, and an inlet tube for nitrogen.

The temperature is brought to 76° C., and after about 1 hour, the reaction mixture is homogeneous and clear. The solvent is removed by under vacuum distillation and the residue which is obtained is distilled at 125° C. and 0.1 mmHg. Acetamide and 1,4-butanediol (20.461 g) are thus recovered. The residue left in the distillation flask (18.237 g) is melted by gentle heating and poured into absolute ethyl alcohol (200 ml). A white precipitate forms which is recovered by filtration and recrystallized from benzene. The thus obtained poly-butyl-oxalate (m.p. 92° C.) is a mixture mainly consisting of dimers and trimers and containing also some higher oligomers. I.R. and NMR analyses confirm the assigned structure.

We claim:

1. A process for the preparation of oxalic acid derivatives of formula (I)

wherein

Z designates an —OR or —NR$^1$R$^2$ group, wherein R represents substituted or unsubstituted alkyl, alkenyl, cycloalkyl, aryl, or aryl-alkyl, R$^1$ is hydrogen or substituted or unsubstituted alkyl, alkenyl, cycloalkyl, aryl, or aryl-alkyl, R$^2$ represents substituted or unsubstituted alkyl, alkenyl, cycloalkyl, aryl, or aryl-alkyl, wherein the R, R$^1$ and R$^2$ substituents are amino, mono-alkylamino, dialkylamino, hydroxy, alkoxy, carboxy, carbalkoxy, formyl, mercapto, alkylthio, cyano, nitro or halogen, or R$^1$ and R$^2$ taken together with the adjacent nitrogen atom represent a saturated 5-, 6-, 7-, or 8-membered heterocyclic ring, which may contain an additional heteroatom selected from —O—, —S—, —N(H,alkyl)—, and optionally bear one or more alkyl or alkenyl substituents, and Z$^1$ designates an —OR or —NR$^1$R$^2$ group, wherein R, R$^1$, and R$^2$ are as defined before, or a group —NHCOCH$_3$, which comprises reacting N,N'-diacetyloxamide (II)

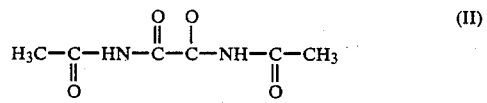

with an alcohol ROH or/and an amine HNR$^1$R$^2$, wherein R, R$^1$ and R$^2$ are as defined above, in the presence of a basic catalyst.

2. The process of claim 1 for the preparation of a compound of formula (I) wherein Z is as defined above and Z$^1$ is —NHCOCH$_3$, characterized in that the alcohol ROH or amine HNR$^1$R$^2$ is employed in equimolar amount with respect to the starting N,N'-diacetyloxamide or in a slight excess thereof.

3. The process of claim 1 for the preparation of a compound of formula (I) wherein Z and Z$^1$ are the same, characterized in that the alcohol ROH or the amine HNR$^1$R$^2$ are employed in at least a double molar amount with respect to the starting N,N'-diacetyloxamide (II).

4. The process of claim 3 wherein the alcohol ROH or the amine $HNR^1R^2$ are employed in an excess with respect to the stoichiometric amount.

5. The process of claim 1 wherein the reaction is carried out at a temperature of from 10° to 100° C.

6. The process of claim 1 for the preparation of a compound of formula (I) wherein Z and $Z^1$ are different and $Z^1$ is different from —$NHCOCH_3$, which comprises reacting a compound of formula II with an equimolar amount or a slight excess of an alcohol ROH or an amine $HNR^1R^2$ wherein R and $R^1$ are as above defined and $R^2$ is —$NHCOCH_3$, in the presence of a basic catalyst.

7. The process of claim 1 wherein the basic catalyst is selected from the group consisting of alkaline alkoxides and nitrogen-containing organic bases.

8. The process of claim 7 wherein the basic catalyst is employed in a molar amount of from 0.0001 to 0.5 per mole of starting amide.

9. The process of claim 8 wherein the amount of basic catalyst is from 0.001 to 0.1 moles per mole of starting amide.

10. The process of any of preceding claims 1 to 6 for the preparation of a compound of formula (I) wherein at least one of Z and $Z^1$ is a —$NR^1R^2$ group, characterized in that the amine $HNR^1R^2$ employed as the reaction partner is also used as the basic catalyst.

11. The process of claim 1, characterized in that the reaction is carried out in the presence of a solvent selected from dimethylacetamide and dimethylformamide.

12. The process of claim 1 characterized in that the reaction is carried out in the presence of a polar, protic or aprotic, organic solvent.

13. The process of claim 12 wherein said organic solvent is selected from cyclic ethers, aliphatic ethers, dietherated glycols, halogenated aliphatic hydrocarbons, organic acid esters, and lower alkanols.

14. The process of claim 1 for the preparation of a compound of formula (I) wherein Z and $Z^1$, which may be equal or different, represent —OR or —$NR^1R^2$ groups, wherein R is substituted or unsubstituted, straight or branched alkly or alkenyl, phenyl or phenyl-($C_1$-$C_4$)alkyl wherein the phenyl ring may be substituted, $R^1$ is hydrogen, substituted or unsubstituted, straight or branched alkyl, substituted or unsubstituted cycloalkyl, phenyl or phenyl-($C_1$-$C_4$)alkyl wherein the phenyl ring may be substituted, $R^2$ is substituted or unsubstituted, straight or branched alkyl, substituted or unsubstituted cycloalkyl, phenyl, or phenyl-($C_1$-$C_4$)alkyl wherein the phenyl group may be substituted, wherein the substituents are amino, monoalkylamino, dialkylamino, hydroxy, alkoxy, carboxy, carbalkoxy, formyl, mercapto, alkylthio, cyano, nitro or halogen, or $R^1$ and $R^2$, taken together with the adjacent nitrogen atom may represent a 5-, 6-, 7-, or 8-membered saturated heterocyclic ring, which may be alkyl- or alkenyl-substituted and optionally contain an additional heteroatom selected from —O—, —S—, or —N(H,Alkyl)—.

15. The process of claim 14 wherein at least one of —R, —$R^1$, and —$R^2$ bears a hydroxy, an amino or a mono-alkyl-amino substituent.

16. The process of claim 15, comprising further reacting compounds of formula (I) with each other, yielding an oligomerization and/or polymerization product.

* * * * *